(12) United States Patent
Zimring et al.

(10) Patent No.: US 10,330,668 B2
(45) Date of Patent: Jun. 25, 2019

(54) BIOCHEMICAL MARKERS OF PLATELET STORAGE

(71) Applicant: Bloodworks, Seattle, WA (US)

(72) Inventors: James Charles Zimring, Seattle, WA (US); Sherrill J. Slichter, Vashon, WA (US)

(73) Assignee: Bloodworks, Seattle, WA (US)

( * ) Notice: Subject to any disclaimer, the term of this patent is extended or adjusted under 35 U.S.C. 154(b) by 496 days.

(21) Appl. No.: 14/906,242

(22) PCT Filed: Jul. 21, 2014

(86) PCT No.: PCT/US2014/047489
§ 371 (c)(1),
(2) Date: Jan. 19, 2016

(87) PCT Pub. No.: WO2015/010137
PCT Pub. Date: Jan. 22, 2015

(65) Prior Publication Data
US 2016/0169866 A1    Jun. 16, 2016

Related U.S. Application Data

(60) Provisional application No. 61/856,645, filed on Jul. 19, 2013.

(51) Int. Cl.
| | | |
|---|---|---|
| *C40B 30/00* | (2006.01) | |
| *G01N 33/53* | (2006.01) | |
| *G01N 33/80* | (2006.01) | |
| *G01N 33/49* | (2006.01) | |
| *G16B 35/00* | (2019.01) | |
| *G16C 20/60* | (2019.01) | |
| *C40B 30/02* | (2006.01) | |

(52) U.S. Cl.
CPC ........... *G01N 33/492* (2013.01); *C40B 30/02* (2013.01); *G01N 33/5308* (2013.01); *G01N 33/80* (2013.01); *G16B 35/00* (2019.02); *G16C 20/60* (2019.02); *G01N 2800/7066* (2013.01)

(58) Field of Classification Search
CPC ................. G01N 33/49; C40B 30/02
See application file for complete search history.

(56) References Cited

U.S. PATENT DOCUMENTS

| | | | | |
|---|---|---|---|---|
| 9,638,687 | B2 * | 5/2017 | Zimring | ................ G01N 33/80 |
| 2003/0215785 | A1 * | 11/2003 | Goodrich | ................ A01N 1/02 |
| | | | | 435/2 |
| 2008/0228456 | A1 | 9/2008 | Clermont et al. | |
| 2011/0003294 | A1 | 1/2011 | Liew | |
| 2011/0151487 | A1 | 6/2011 | D'Andrea et al. | |
| 2011/0229883 | A1 | 9/2011 | Spur et al. | |
| 2013/0288387 | A1 | 10/2013 | Blancher et al. | |
| 2014/0343865 | A1 * | 11/2014 | Brown | ............... G01N 33/5011 |
| | | | | 702/19 |

OTHER PUBLICATIONS

Uathavikul et al., Metabolic Changes and Viability of Stored Human Platelets, Journal of Clinical Investigation, 1962, 41(6), 1334-1414. (Year: 1962).*
Vangaveti et al., Hydroyoctadecadienoic Acids: Novel Regulators of Macrophage Differentiation and Atherogenesis, Therapeutic Advances in Endocrinology and Metabolism, 2010, 1(2), 51-60. (Year: 2010).*
PCT International Search Report and Written Opinion, PCT Application No. PCT/US14/47489, dated Jan. 21, 2015, 18 pages.
PCT Invitation to Pay Additional Fees, PCT Application No. PCT/US14/47489, dated Oct. 30, 2014, 3 pages.
Zimring, et al., "Metabolites in stored platelets associated with platelet recoveries and survivals," Transfusion, vol. 56, 2016, 10 pages.

* cited by examiner

*Primary Examiner* — Amy M Bunker
(74) *Attorney, Agent, or Firm* — Lee & Hayes PC; C. Rachal Winger; Thu Nguyen

(57) ABSTRACT

Compositions and methods determines post-transfusion survival of platelets and the suitability of platelet units for transfusion by measuring the levels of one or more markers in a platelet sample. A method determines post-transfusion survival of platelets (PL T) prior to transfusion, the method comprising the steps of: a) measuring the levels of one or more markers in a PL T sample selected from the group consisting of adenine, 13-HODE/9-HODE, Caprylate, Laurate, C-glycosyltryptophan, andro steroid monsulfate 2, and Unelucidated Compounds (UC) 1-4; b) comparing the level of the one or more markers in the PLT sample with the level of the one or more markers present in a control sample, wherein a higher or lower level of the one or more markers in the PL T sample is indicative of post-transfusion survival of platelets.

12 Claims, 5 Drawing Sheets

BIOCHEMICAL MARKERS OF PLATELET STORAGE

CROSS-REFERENCE TO RELATED APPLICATIONS

This application is a U.S. National Phase application based on PCT/US2014/047489, filed Jul. 21, 2014, which claims the benefit of priority to U.S. Provisional Patent Application No. 61/856,645, filed Jul. 19, 2013, each of which is incorporated herein by reference in its entirety as if fully set forth herein.

FIELD

The invention relates to compositions and methods for determining post-transfusion survival of platelets (PLT), efficacy of PLTs, and potential untoward toxicities of PLTs, by measuring the levels of one or more markers in a PLT sample.

BACKGROUND

In excess of 4,000,000 units of platelets (PLTs) are transfused annually in the United States. Currently, there are only 3 quality control measures utilized prior to release of a unit of PLTs: 1) the absence of screened pathogens, 2) visual assessment for swirling and the presence of visual abnormalities suggestive of bacterial contamination (with or without formal bacterial screening), 3) storage history of agitation and temperature control. However, it has been known for decades that the quality of PLTs can vary widely from unit to unit and from donor to donor. Indeed, transfusion of certain units may result in substantial increases in recipient circulating platelets, whereas other units give no discernable benefit. However, the factors that regulate whether PLTs collected from a given donor store well or not is poorly understood. For this reason, currently, there are no quality control measures related to the extent to which a transfused unit of PLTs will survive post-transfusion. This is a medical problem since PLTs that survive poorly post-transfusion result in a less efficacious product from the standpoint of PLT replacement. Collection and transfusing of PLTs is an expensive and time consuming process, and the inability to distinguish which units and/or which donors will not result in an efficacious unit results in a substantial waste of medical resources.

Disclosed herein is a method for assessing a PLT unit (prior to transfusion) allowing the prediction of its post-transfusion survival and also potential toxicity. Specifically, biochemical markers that predict if PLTs will survive well post-transfusion are presented herein.

SUMMARY

Described herein are compositions and methods for determining post-transfusion survival of a platelet (PLT) unit by measuring the levels of one or more markers in a PLT sample.

In a first aspect, disclosed herein is a method of determining post-transfusion survival of platelets (PLT) prior to transfusion, the method comprising the steps of: a) measuring the levels of one or more markers in a PLT sample selected from the group consisting of adenine, 13-HODE/9-HODE, Caprylate, Laurate, C-glycosyltryptophan, andro steroid monosulfate 2, and Unelucidated Compounds (UC) 1-4; b) comparing the level of the one or more markers in the PLT sample with the level of the one or more markers present in a control sample, wherein a higher or lower level of the one or more markers in the PLT sample is indicative of post-transfusion survival of platelets.

In a second aspect, disclosed herein is a method of determining the suitability of a platelet (PLT) unit for transfusion, the method comprising the steps of: a) measuring the levels of one or more markers in a PLT sample selected from the group consisting of adenine, 13-HODE/9-HODE, Caprylate, Laurate, C-glycosyltryptophan, andro steroid monosulfate 2, and Unelucidated Compounds (UC) 1-4; b) comparing the level of the one or more markers in the PLT sample with the level of the one or more markers present in a control sample, wherein a higher or lower level of the one or more markers in the PLT sample is indicative of suitability for transfusion.

In an embodiment, the levels of the one or more markers in the PLT sample is indicative of the level of leukotrienes or prostaglandins in the PLT sample, thereby indicating the suitability of the sample for transfusion.

In various embodiments of the first and second aspects, the measurement is performed at the time of collection of the PLT sample.

In various embodiments of the first and second aspects, the measurement is performed during the time of storage of the PLT sample.

In various embodiments of the first and second aspects, the measurement is performed by mass spectrometry. In various embodiments, the mass spectrometry is gas-chromatography/mass spectrometry (GC/MS) or liquid chromatography-tandem mass spectrometry (LC/MS/MS).

In various embodiments of the first and second aspects, the measurement is performed by enzymatic assay.

In various embodiments of the first and second aspects, the measurement is performed by ELISA.

In various embodiments of the first and second aspects, the level of the one or more marker is 2-200 fold higher than in the control sample.

In a third aspect, disclosed herein is method for determining PLT storage quality, the method comprising the steps of: obtaining a dataset associated with a sample of stored platelets, wherein the dataset comprises at least one marker, selected from the group consisting of adenine, 13-HODE/9-HODE, Caprylate, Laurate, C-glycosyltryptophan, andro steroid monosulfate 2, and Unelucidated Compounds (UC) 1-4; analyzing the dataset to determine data for the at least one marker, wherein the data is positively correlated or negatively correlated with PLT storage quality of the sample of stored platelets.

In a fourth aspect, disclosed herein is method for determining PLT storage quality, the method comprising the steps of: obtaining a sample of stored platelets, wherein the sample comprises at least one marker, selected from the group consisting of adenine, 13-HODE/9-HODE, Caprylate, Laurate, C-glycosyltryptophan, andro steroid monosulfate 2, and Unelucidated Compounds (UC) 1-4; contacting the sample with a reagent; generating a complex between the reagent and the at least one marker; detecting the complex to obtain a dataset associated with the sample, wherein the dataset comprises expression or activity level data for the at least one marker; and analyzing the expression or activity level data for the at least one marker, wherein the expression or activity level of the at least one marker is positively correlated or negatively correlated with PLT storage quality.

In a fifth aspect, disclosed herein is computer-implemented method for determining PLT storage quality, the method comprising the steps of: storing, in a storage memory, a dataset associated with a stored platelet sample, wherein the dataset comprises data for at least one marker, selected from the group consisting of adenine, 13-HODE/9-HODE, Caprylate, Laurate, C-glycosyltryptophan, andro steroid monosulfate 2, and Unelucidated Compounds (UC) 1-4; and analyzing, by a computer processor, the dataset to determine the expression or activity levels of the at least one marker, wherein the expression or activity levels are positively correlated or negatively correlated with PLT storage quality.

In a sixth aspect, disclosed herein is system for determining PLT storage quality, the system comprising: a storage memory for storing a dataset associated with a stored platelet sample, wherein the dataset comprises data for at least one marker, wherein the dataset comprises data for at least one marker, selected from the group consisting of adenine, 13-HODE/9-HODE, Caprylate, Laurate, C-glycosyltryptophan, andro steroid monosulfate 2, and Unelucidated Compounds (UC) 1-4; and a processor communicatively coupled to the storage memory for analyzing the dataset to determine the activity or expression levels of the at least one marker, wherein the activity or expression levels are positively correlated or negatively correlated with PLT storage quality.

In a seventh aspect, disclosed herein is computer-readable storage medium storing computer-executable program code, the program code comprising: program code for storing a dataset associated with a stored platelet sample, wherein the dataset comprises data for at least one marker, wherein the dataset comprises data for at least one marker, selected from the group consisting of adenine, 13-HODE/9-HODE, Caprylate, Laurate, C-glycosyltryptophan, andro steroid monosulfate 2, and Unelucidated Compounds (UC) 1-4; and program code for analyzing the dataset to determine the activity or expression levels of the at least one marker, wherein the activity or expression levels of the markers are positively correlated or negatively correlated with PLT storage quality.

In an eighth aspect, disclosed herein is method for predicting transfusion outcome, the method comprising the steps of: obtaining a dataset associated with a sample of stored platelets, wherein the dataset comprises at least one marker, wherein the dataset comprises data for at least one marker, selected from the group consisting of adenine, 13-HODE/9-HODE, Caprylate, Laurate, C-glycosyltryptophan, andro steroid monosulfate 2, and Unelucidated Compounds (UC) 1-4; analyzing the dataset to determine data for the at least one marker, wherein the data is positively correlated or negatively correlated with transfusion outcome if the platelet sample is transfused into a patient.

In a ninth aspect, disclosed herein is method for predicting transfusion outcome, the method comprising the steps of: obtaining a sample of stored platelets, wherein the sample comprises at least one marker, wherein the dataset comprises data for at least one marker, selected from the group consisting of adenine, 13-HODE/9-HODE, Caprylate, Laurate, C-glycosyltryptophan, andro steroid monosulfate 2, and Unelucidated Compounds (UC) 1-4; contacting the sample with a reagent; generating a complex between the reagent and the at least one marker; detecting the complex to obtain a dataset associated with the sample, wherein the dataset comprises expression or activity level data for the at least one marker; and analyzing the expression or activity level data for the markers, wherein the expression or activity level of the at least one marker is positively correlated or negatively correlated with transfusion outcome if the platelet sample is transfused into a patient.

In a tenth aspect, disclosed herein is computer-implemented method for predicting transfusion outcome, the method comprising the steps of: storing, in a storage memory, a dataset associated with a stored platelet sample, wherein the dataset comprises data for at least one marker wherein the dataset comprises data for at least one marker, selected from the group consisting of adenine, 13-HODE/9-HODE, Caprylate, Laurate, C-glycosyltryptophan, andro steroid monosulfate 2, and Unelucidated Compounds (UC) 1-4; and analyzing, by a computer processor, the dataset to determine the expression or activity levels of the at least one marker, wherein the expression or activity levels are positively correlated or negatively correlated with transfusion outcome if the platelet sample is transfused into a patient.

In an eleventh aspect, disclosed herein is system for predicting transfusion outcome, the system comprising: a storage memory for storing a dataset associated with a stored platelet sample, wherein the dataset comprises data for at least one marker, wherein the dataset comprises data for at least one marker, selected from the group consisting of adenine, 13-HODE/9-HODE, Caprylate, Laurate, C-glycosyltryptophan, andro steroid monosulfate 2, and Unelucidated Compounds (UC) 1-4; and a processor communicatively coupled to the storage memory for analyzing the dataset to determine the activity or expression levels of the at least one marker, wherein the activity or expression levels are positively correlated or negatively correlated with transfusion outcome if the platelet sample is transfused into a patient.

In a twelfth aspect, disclosed herein is computer-readable storage medium storing computer-executable program code, the program code comprising: program code for storing a dataset associated with a stored platelet sample, wherein the dataset comprises data for at least one marker, selected from the group consisting of adenine, 13-HODE/9-HODE, Caprylate, Laurate, C-glycosyltryptophan, andro steroid monosulfate 2, and Unelucidated Compounds (UC) 1-4; and program code for analyzing the dataset to determine the activity or expression levels of the at least one marker, wherein the activity or expression levels of the markers are positively correlated or negatively correlated with transfusion outcome if the platelet sample is transfused into a patient.

In various embodiments of the above aspects, the dataset is obtained at the time of collection of the PLT sample.

In various embodiments of the above aspects, the dataset is obtained during the time of storage of the PLT sample.

In various embodiments of the above aspects, the dataset is obtained by mass spectrometry.

In various embodiments of the above aspects, the mass spectrometry is gas-chromatography/mass spectrometry (GC/MS) or liquid chromatography-tandem mass spectrometry (LC/MS/MS).

In various embodiments of the above aspects, the dataset is obtained by enzymatic assay.

In various embodiments of the above aspects, the dataset is obtained by ELISA.

In a thirteenth aspect, disclosed herein is kit for use in predicting transfusion outcome or platelet (PLT) storage quality, the kit comprising: a set of reagents comprising a plurality of reagents for determining from a stored platelet sample data for at least one marker, selected from the group consisting of adenine, 13-HODE/9-HODE, Caprylate, Laurate, C-glycosyltryptophan, andro steroid monosulfate 2, and Unelucidated Compounds (UC) 1-4; and instructions for using the plurality of reagents to determine data from the stored platelet sample.

DETAILED DESCRIPTION

Figure 1:
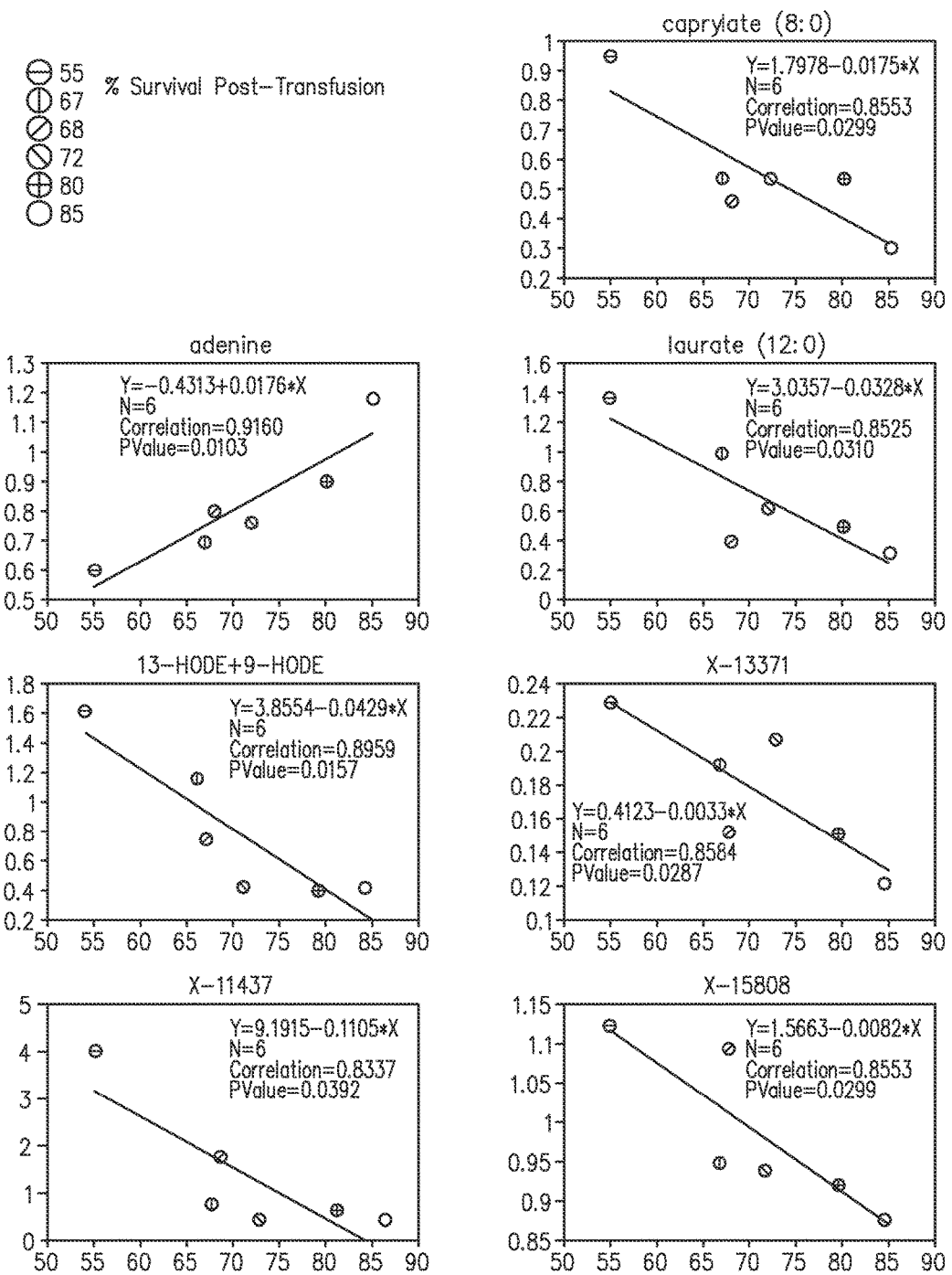
FIG. 1. Correlation of relative amounts of analyte (y-axis) with post-transfusion survival of platelets. The included analytes were detected at time of collection or at day 1 of storage. Platelets were transfused and post-transfusion survival data were obtained on day 5. Accordingly, the correlations presented in FIG. 1 represent analytes that predict from early time points how platelets will perform subsequently.
Figure 2:
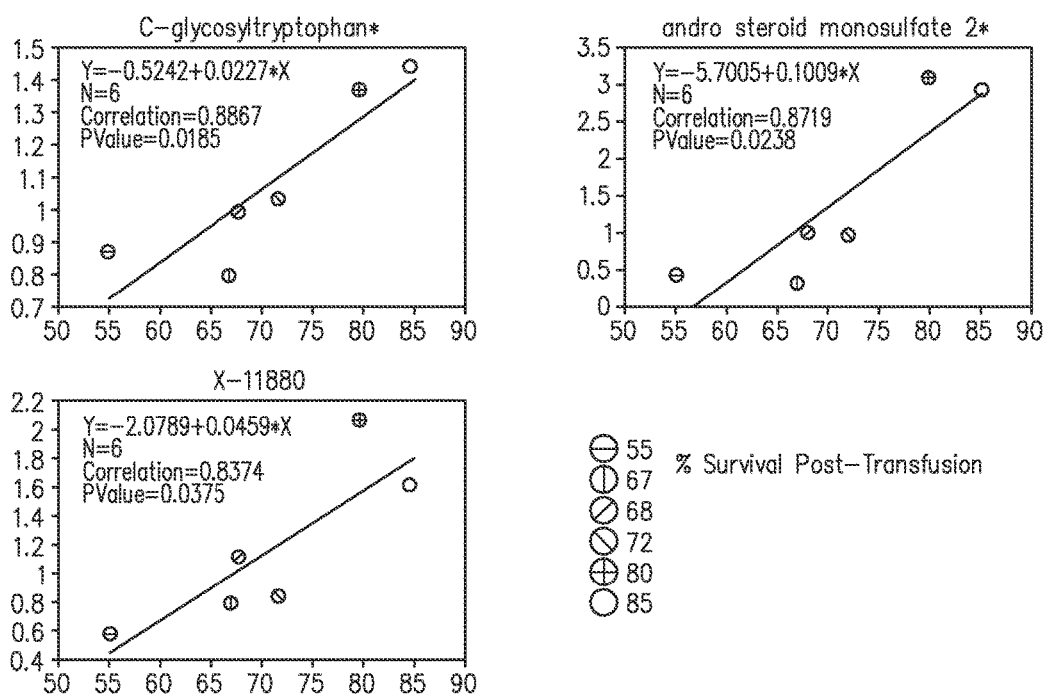
FIG. 2. Correlates of relative amounts of analyte (y-axis) with post-transfusion survival of platelets. The included analytes were detected late in storage, and thus generate a profile over storage time that predicts ultimate platelet performance upon transfusion.
Figure 3:
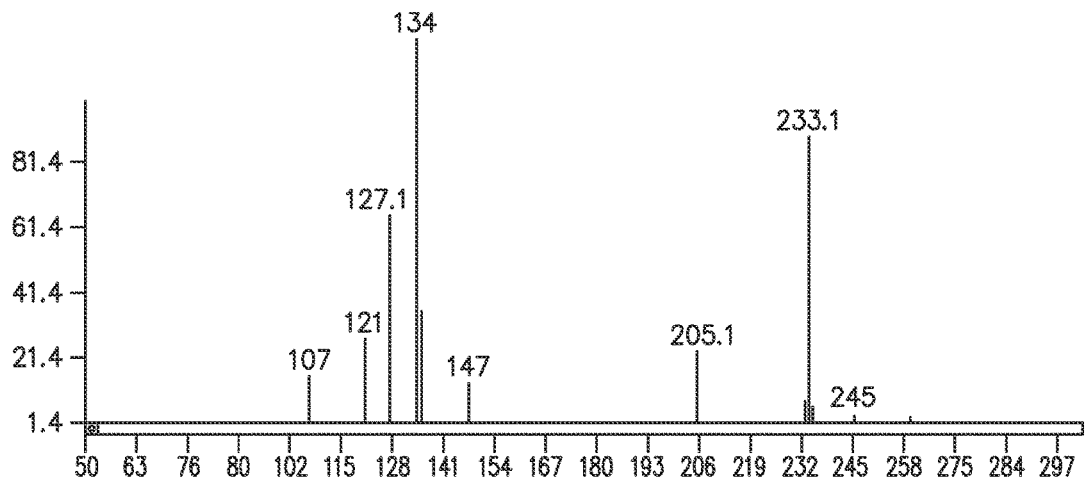
FIG. 3. Mass spectrometry data for unelucidated structure X-13371.
Figure 4:
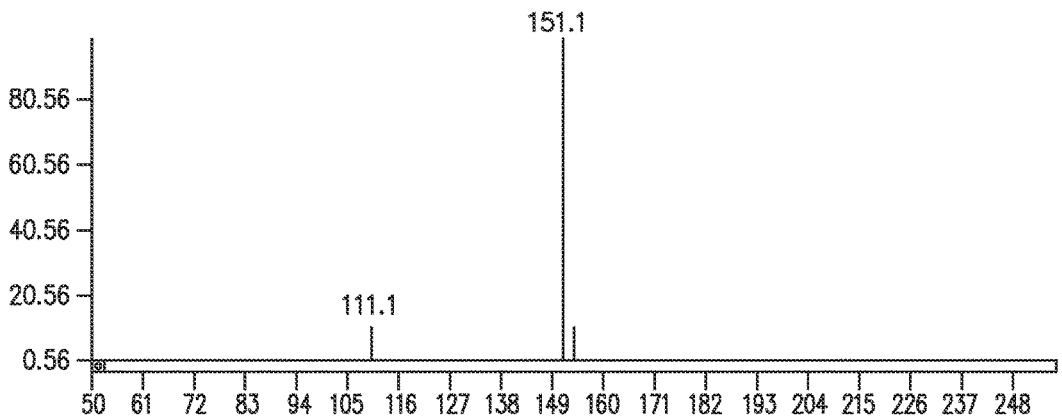
FIG. 4. Mass spectrometry data for unelucidated structure X-11437.
Figure 5:
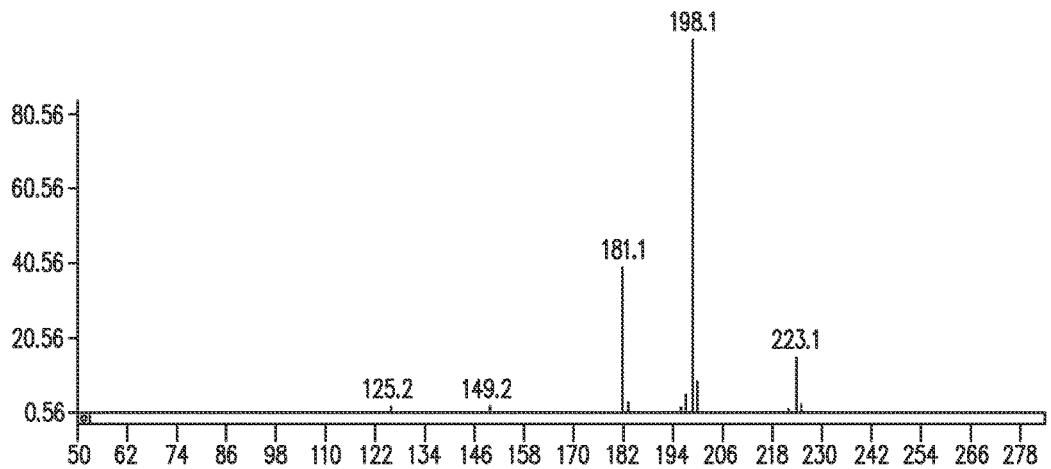
FIG. 5. Mass spectrometry data for unelucidated structure X-15808.
Figure 6:
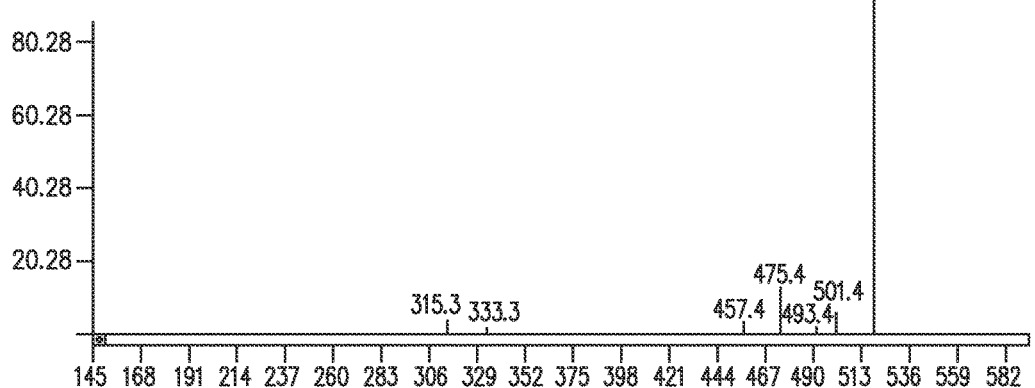
FIG. 6. Mass spectrometry data for unelucidated structure X-11880.
Figure 7:
FIG. 7. Mass spectrometry data for unelucidated structure X-14577.

The present invention generally relates to compositions and methods for determining post-transfusion survival of platelets (PLT) by measuring the levels of one or more markers in a PLT sample.

It is to be understood that this invention is not limited to particular methods, reagents, compounds, compositions or biological systems, which can, of course, vary. It is also to be understood that the terminology used herein is for the purpose of describing particular aspects only, and is not intended to be limiting. As used in this specification and the appended claims, the singular forms "a", "an" and "the" include plural references unless the content clearly dictates otherwise.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

An "analyte" or "target" refers to a compound to be detected. Such compounds can include small molecules, peptides, proteins, nucleic acids, as well as other chemical entities. In the context of the present invention, an analyte or target will generally correspond to the biochemical compounds disclosed herein, or a reaction product thereof.

The term "biomarker" refers to a molecule (typically small molecule, protein, nucleic acid, carbohydrate, or lipid) that is expressed and/or released from a cell, which is useful for identification or prediction. Such biomarkers are molecules that can be differentially expressed, e.g., overexpressed or underexpressed, or differentially released in response to varying conditions (e.g., storage). In the context of the present invention, this frequently refers to the biochemical compounds disclosed herein, which are elevated in stored versus non-stored platelets, for instance, 1-fold, 2-fold, 3-fold, 4-fold, 5-fold or more in stored platelets versus non-stored platelets.

A "sample" refers to any source which is suspected of containing an analyte or target molecule. Examples of samples which may be tested using the present invention include, but are not limited to, blood, serum, plasma, urine, saliva, cerebrospinal fluid, lymph fluids, tissue and tissue and cell extracts, cell culture supernatants, among others. A sample can be suspended or dissolved in liquid materials such as buffers, extractants, solvents, and the like. In the context of the present application, a sample is generally a stored platelet sample of varying length of storage.

"Antibody" refers to any immunoglobulin or intact molecule as well as to fragments thereof that bind to a specific epitope that may be used in the practice of the present invention. Such antibodies include, but are not limited to polyclonal, monoclonal, chimeric, humanized, single chain, Fab, Fab', F(ab)' fragments and/or F(v) portions of the whole antibody and variants thereof. All isotypes are encompassed by this term and may be used in the practice of this invention, including IgA, IgD, IgE, IgG, and IgM.

An "antibody fragment" refers specifically to an incomplete or isolated portion of the full sequence of the antibody which retains the antigen binding function of the parent antibody and may also be used in the present invention. Examples of antibody fragments include Fab, Fab', F(ab')2, and Fv fragments; diabodies; linear antibodies; single-chain antibody molecules; and multispecific antibodies formed from antibody fragments.

An intact "antibody" for use in the invention comprises at least two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system. The term antibody includes antigen-binding portions of an intact antibody that retain capacity to bind. Examples of binding include (i) a Fab fragment, a monovalent fragment consisting of the $V_L$, $V_H$, $C_L$ and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the $V_L$ and $V_H$ domains of a single arm of an antibody, (v) a dAb fragment (Ward et al., Nature, 341:544-546 (1989)), which consists of a VH domain; and (vi) an isolated complementarity determining region (CDR).

"Single chain antibodies" or "single chain Fv (scFv)" may also be used in the present invention. This term refers to an antibody fusion molecule of the two domains of the Fv fragment, $V_L$ and $V_H$. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., Science, 242:423-426 (1988); and Huston et al., Proc Natl Acad Sci USA, 85:5879-5883 (1988)). Such single chain antibodies are included by reference to the term "antibody" fragments can be prepared by recombinant techniques or enzymatic or chemical cleavage of intact antibodies.

A "monoclonal antibody" may be used in the present invention. Monoclonal antibodies are a preparation of antibody molecules of single molecular composition. A monoclonal antibody composition displays a single binding specificity and affinity for a particular epitope.

In one embodiment, the antibody or fragment is conjugated to an "effector" moiety. The effector moiety can be any number of molecules, including labeling moieties such as radioactive labels or fluorescent labels.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

Samples of platelets stored for various amounts of time are compared to "control" samples which can be freshly drawn platelets or platelets which have been minimally stored. Control samples are assigned a relative analyte amount or activity to which sample values are compared. Relevant levels of analyte elevation occur when the sample amount or activity value relative to the control is 110%, more preferably 150%, more preferably 200-500% (i.e., two to five fold higher relative to the control), more preferably 1000-3000% higher.

As used herein, "PLT storage quality" is defined as the extent of post-transfusion recovery of the stored PLTs; higher recovery is defined as higher quality. Examples of post-transfusion recovery include greater than zero and almost 100% recovery, i.e., recovery of 10%, 20%, 30%, 40%, 50%, 60%, 70%, 80%, 90%, 100%, and all percentages in between.

As used herein, "toxicity" of a PLT unit is defined as any adverse reaction associated with transfusion of a PLT unit, including, but not limited to, fever, inflammation, induction of recipient cytokines, transfusion induced lung injury, and transfusion-related immunomodulation, among others.

As used herein, a PLT unit is less suitable for transfusion if it has lower PLT quality (i.e., post-transfusion survival) or elevated toxicity as compared to other PLT units, e.g., as compared to a control.

As used herein, "transfusion outcome" refers to post-transfusion survival of platelets in the circulation and the presence or absence of toxicity after platelet transfusion.

Assays for many of the biochemical compounds disclosed herein are known or commercially available.

For example, antibody reagents can be used in assays to detect the levels of analytes in platelet samples using any of a number of immunoassays known to those skilled in the art.

Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used. See, e.g., Self et al., Curr. Opin. Biotechnol., 7:60-65 (1996). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (META); immunohistochemical (IHC) assays; capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence. See, e.g., Schmalzing et al., Electrophoresis, 18:2184-93 (1997); Bao, J. Chromatogr. B. Biomed. Sci., 699:463-80 (1997). Liposome immunoassays, such as flow-injection liposome immunoassays and liposome immunosensors, are also suitable for use in the present invention. See, e.g., Rongen et al., J. Immunol. Methods, 204:105-133 (1997). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., J. Clin. Chem. Clin. Biochem., 27:261-276 (1989)).

Specific immunological binding of the antibody to proteins can be detected directly or indirectly. Direct labels include fluorescent or luminescent tags, metals, dyes, radionuclides, and the like, attached to the antibody. A chemiluminescence assay using a chemiluminescent antibody specific for the protein is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}I$; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

In some embodiments, the measurement of the markers of the present invention is performed using various mass spectrometry methods. As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., Prostate Cancer and Prostatic Diseases 1999, 2: 264-76; and Merchant and Weinberger, Electrophoresis 2000, 21; 1164-67.

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

In some embodiments, the present invention is practiced using computer implementation. In one embodiment, a computer comprises at least one processor coupled to a chipset. Also coupled to the chipset are a memory, a storage device, a keyboard, a graphics adapter, a pointing device, and a network adapter. A display is coupled to the graphics adapter. In one embodiment, the functionality of the chipset is provided by a memory controller hub and an I/O controller hub. In another embodiment, the memory is coupled directly to the processor instead of the chipset.

The storage device is any device capable of holding data, like a hard drive, compact disk read-only memory (CD-ROM), DVD, or a solid-state memory device. The memory holds instructions and data used by the processor. The pointing device may be a mouse, track ball, or other type of pointing device, and is used in combination with the keyboard to input data into the computer system. The graphics adapter displays images and other information on the display. The network adapter couples the computer system to a local or wide area network.

As is known in the art, a computer can have different and/or other components than those described previously. In addition, the computer can lack certain components. Moreover, the storage device can be local and/or remote from the computer (such as embodied within a storage area network (SAN)).

As is known in the art, the computer is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device, loaded into the memory, and executed by the processor.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

The following examples of specific aspects for carrying out the present invention are offered for illustrative purposes only, and are not intended to limit the scope of the present invention in any way.

EXAMPLES

Example 1: Methods

Donor PLT samples, freshly obtained and at various times after storage, were rapidly frozen using dry ice/ethanol and stored at 80° C. The supernatant was not stored separately nor were the PLTs washed and stored separately; thus, the results obtained evaluated the metabolites in the entire "unit." Samples were split into equal parts for analysis by gas-chromatography/mass spectrometry (GC/MS) and liquid chromatography-tandem mass spectrometry (LC/MS/MS). The LC/MS/MS platform was based on a Waters ACQUITY UPLC and a Thermo-Finnigan LTQ mass spectrometer, which consisted of an electrospray ionization (ESI) source and linear ion-trap (LIT) mass analyzer. The sample extract was split into two aliquots, dried, and then reconstituted in acidic or basic LC-compatible solvents, each of which contained 11 or more injection standards at fixed concentrations. One aliquot was analyzed using acidic positive-ion optimized conditions and the other using basic negative-ion optimized conditions in two independent injections using separate dedicated columns. Extracts reconstituted in acidic conditions were gradient eluted using water and methanol, both containing 0.1% Formic acid, whereas the basic extracts, which also used water/methanol, contained 6.5 mM Ammonium Bicarbonate. The MS analysis alternated between MS and data-dependent $MS^2$ scans using dynamic exclusion. The samples destined for GC/MS analysis were re-dried under vacuum desiccation for a minimum of 24 hr prior to being derivatized under dried nitrogen using bistrimethyl-silyl-triflouroacetamide. The GC column was 5% phenyl and the temperature ramp was from 40° to 300° C. in a 16 minute period. Samples were analyzed on a Thermo-Finnigan Trace DSQ fast-scanning single-quadrupole mass spectrometer using electron impact ionization. Compounds were identified by comparison to library entries of purified standards or recurrent unknown entities. Identification of known chemical entities was based on comparison to metabolomic library entries of purified standards. As of the time of analysis, more than 1000 commercially-available purified standard compounds had been acquired and registered into LIMS for distribution to both the LC and GC platforms for determination of their analytical characteristics. The combination of chromatographic properties and mass spectra gave an indication of a match to the specific compound or an isobaric entity.

The peak areas for each identified biochemical entity were log transformed, scaled to the median value for each compound observed in the experiment, and normalized to Bradford protein content; results below the limit of detection were imputed with the minimum observed value for the compound. A Two-Way ANOVA with Contrasts was used to determine the significance of variable main effects (e.g. Condition or Time/Day) and their interaction, and to identify biochemical entities that differed significantly between experimental groups (p≤0.05). An estimate of the false discovery rate (q-value) is calculated to take into account the multiple comparisons that normally occur in metabolomic-based studies.

Example 2: Determination of Biochemical Markers of Platelet Storage

We have performed an extensive metabolic analysis of stored PLTs, collected from human donors. For each unit studied, post-transfusion survival was determined in human volunteers by infusing autologous radiolabeled PLTs and measuring circulatory life span. Correlation coefficients were calculated for post-transfusion PLT survival vs. each of over 400 detected metabolites. As a result of these studies, we have identified a distinct panel of metabolites that correlate with how well PLTs survive post-transfusion.

Specifically, leukoreduced apheresis PLTs were collected from healthy human subjects and stored for 8 days. Aliquots were taken on days 0, 1, 3, 5, and 8, stored at −80° C., and subsequently analyzed by LC-MS/MS and GC-MS. After 5 days storage, a PLT sample was removed and a sample of fresh PLTs was obtained from the same donor. The stored and fresh PLTs were labeled with either $^{51}Cr$ or $^{111}In$ prior to transfusion. Post-transfusion survival was calculated as a ratio of stored to fresh PLT survivals.

332 identified compounds and 86 Unelucidated Compounds (UC) were quantified. Consistent with existing literature, lactate increased over time while ADP and serotonin decreased. Metabolomic analysis of stored PLTs showed: (1) Increased amino acids and organic osmolytes leading to potential osmotic stress. (2) Evidence of oxidative tress due to decreased cysteine and cysteine-glutathione disulfide and increased 2-aminobutyrate 5-oxoproline, markers of transulfuration pathway activity and glutathione turnover. (3) Lipid breakdown indicated by elevation of indicators of both lipolysis and phospholipid catabolism, suggesting dysregulation of energy metabolism. (4) Accumulation of fatty acid beta-oxidation intermediates, acylcarnitines and Krebs cycle intermediates, suggesting a Krebs cycle blockage and mitochondrial dysfunction. When the Krebs cycle's capacity to use pyruvate is overwhelmed, pyruvate is converted to lactate. Thus, these findings provide mechanistic insight into lactate accumulation and pH drop. Correlation coefficients (CC) were calculated for all analytes compared to post-transfusion survival.

Significant correlations were observed between levels at time of collection and PLT survival, including adenine (CC=0.95, p=0.004), UC1 [X-13371] (CC=0.87, p=0.02), 13-HODE/9-HODE (CC=−0.9, p=0.016), UC2 [x-11437] (CC=−0.86, p=0.03), caprylate (CC=−0.86, p=0.03). Laurate levels correlated to PLT survival at time of collection and until day 5 of storage (CC=−0.84, p=0.04). Other compounds had no significant correlation at time of collection, but developed a significant correlation (with ultimate PLT survival) over the time course of storage, including C-glycosyltryptophan, andro steroid monosulfate 2, and UC3 [x-15808] and UC4 [x-11880].

Accordingly, the identified panel includes, at least, the following biochemicals.
1. adenine
2. 13-HODE/9-HODE
3. Caprylate
4. Laurate
5. C-glycosyltryptophan
6. Andro steroid monosulfate 2
7. Unelucidated Compounds 1-4

Example 3: Application of the Above Markers as a Diagnostic Test of PLT Analysis The above markers of PLT unit quality may be applied to the evaluation of PLT units in several different ways. First, a sample of a PLT unit can be subjected to mass spectrometry and the profile of the above markers can be generated (all from a single sample). This profile would then be used to predict the post-transfusion survival of a PLT unit. Such information would allow 3 distinct medical advantages: 1) direction of better units of PLTs to patients whose disease status makes them particularly susceptible to bleeding from thrombocytopenia, 2) management of the blood supply such that donors with good storage properties can be preferentially recruited, 3) decrease the number of units any given patient receives, thereby decreasing exposure to multiple donors and deceasing risk of both alloimmunization and infectious disease transmission, and 4) identification of PLT units with lower leukotrienes and prostaglandins, thus allowing units with higher amounts of such substances to not be transfused into patients predicted to be sensitive to such substances. Alternatively, individual assays could be run on a much smaller platform by traditional assay techniques (i.e. ELISA, enzymatic assay, etc.). Such would allow a simplified platform with a less expensive instrumentation. For such purposes, a small number of the above chemical entities that were representative of the whole would be identified and measured.

While specific aspects of the invention have been described and illustrated, such aspects should be considered illustrative of the invention only and not as limiting the invention as construed in accordance with the accompanying claims.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed:

1. A method of determining post-transfusion survival of platelets (PLT) prior to transfusion, the method comprising:
   a) obtaining a test aliquot from a leukoreduced apheresis platelet (PLT) unit obtained from a human;
   b) obtaining a control aliquot from a control leukoreduced apheresis PLT unit, wherein the control leukoreduced apheresis PLT unit is obtained from a healthy human subject, and wherein the control aliquot is tested at the time of collection and at multiple time points during storage of the control leukoreduced apheresis PLT unit;
   c) using an assay to measure in the test aliquot and in the control aliquot a level of one or more biomarkers selected from the group consisting of adenine, 13-hydroxyoctadecadienoic acid/9-hydroxyoctadecadienoic acid (13-HODE/9-HODE), caprylate, laurate, C-glycosyltryptophan, and andro steroid monosulfate 2;
   d) comparing the levels of the one or more biomarkers in the test aliquot with the levels of the same one or more corresponding biomarkers present in the control aliquot; and
   e) determining that the leukoreduced apheresis PLT unit is suitable for transfusion when there is a statistically significant increase in the levels of one or more of the biomarkers selected from the group consisting of adenine, C-glycosyltryptophan, and andro steroid monosulfate 2 in the test aliquot as compared to the corresponding levels of the same biomarkers in the control aliquot, and/or when there is a statistically significant decrease in the levels of one or more of the biomarkers selected from the group consisting of 13-HODE/9-HODE, caprylate, and laurate in the test aliquot as compared to the corresponding levels of the same biomarkers in the control aliquot; or
   f) determining that the leukoreduced apheresis PLT unit is unsuitable for transfusion when there is a statistically significant decrease in the levels of one or more of the biomarkers selected from the group consisting of adenine, C-glycosyltryptophan, and andro steroid monosulfate 2 in the test aliquot as compared to the corresponding levels of the same biomarkers in the control aliquot, and/or when there is a statistically significant increase in the levels of the one or more biomarkers selected from the group consisting of 13-HODE/9-HODE, caprylate, and laurate in the test aliquot as compared to the corresponding levels of the same biomarkers in the control aliquot; and
   g) releasing the leukoreduced apheresis PLT unit for transfusion when step (e) is indicated, or
   h) not releasing the leukoreduced apheresis PLT unit for transfusion when step (f) is indicated, wherein a higher or a lower level of the one or more biomarkers in the PLT sample is indicative of post-transfusion survival of platelets.

2. The method of claim 1, wherein the measurements on the test aliquot are performed at the time the PLT unit is obtained from the human.

3. The method of claim 1, wherein the measurements on the test aliquot are performed during the time that the PLT unit obtained from the human has been stored.

4. The method of claim 1, wherein the measurements performed are selected from the group consisting of mass spectrometry, enzymatic assay, and enzyme-linked immunosorbent assay (ELISA).

5. The method of claim 4, wherein the measurements are performed by a mass spectrometry technique selected from the group consisting of gas-chromatography/mass spectrometry (GC/MS), and liquid chromatography-tandem mass spectrometry (LC/MS/MS).

6. The method of claim 1, wherein the levels of the one or more biomarkers selected from the group consisting of adenine, C-glycosyltryptophan, and andro steroid monosulfate 2 in the test aliquot are 2-200 fold higher than the corresponding levels of the same biomarkers in the control aliquot.

7. A method, comprising:
   a) obtaining a test aliquot from a leukoreduced apheresis platelet (PLT) unit obtained from a human;
   b) obtaining a control aliquot from a control leukoreduced apheresis PLT unit, wherein the control leukoreduced apheresis PLT unit is obtained from a healthy human subject, and wherein the control aliquot is tested at the time of collection and at multiple time points during storage of the control leukoreduced apheresis PLT unit;
   c) using an assay to measure in the test aliquot and in the control aliquot a level of one or more biomarkers selected from the group consisting of adenine, 13-hydroxyoctadecadienoic acid/9-hydroxyoctadecadienoic acid (13-HODE/9-HODE), caprylate, laurate, C-glycosyltryptophan, and andro steroid monosulfate 2;
   d) comparing the levels of the one or more biomarkers in the test aliquot with the levels of the same one or more corresponding biomarkers present in the control aliquot; and
   e) determining that the leukoreduced apheresis PLT unit is suitable for transfusion when there is a statistically significant increase in the levels of one or more of the biomarkers selected from the group consisting of adenine, C-glycosyltryptophan, and andro steroid monosulfate 2 in the test aliquot as compared to the corresponding levels of the same biomarkers in the control aliquot, and/or when there is a statistically significant decrease in the levels of one or more of the biomarkers selected from the group consisting of 13-HODE/9-HODE, caprylate, and laurate in the test aliquot as compared to the corresponding levels of the same biomarkers in the control aliquot; or
   f) determining that the leukoreduced apheresis PLT unit is unsuitable for transfusion when there is a statistically significant decrease in the levels of one or more of the biomarkers selected from the group consisting of adenine, C-glycosyltryptophan, and andro steroid monosulfate 2 in the test aliquot as compared to the corresponding levels of the same biomarkers in the control aliquot, and/or when there is a statistically significant increase in the levels of the one or more biomarkers selected from the group consisting of 13-HODE/9-HODE, caprylate, and laurate in the test aliquot as compared to the corresponding levels of the same biomarkers in the control aliquot; and g) transfusing the leukoreduced apheresis PLT unit into a human when step (e) is indicated, or h) not transfusing the leukoreduced apheresis PLT unit into a human when step (f) is indicated.

8. The method of claim 7, wherein the measurements on the test aliquot are performed at the time the leukoreduced apheresis PLT unit is obtained from the human.

9. The method of claim 7, wherein the measurements on the test aliquot are performed during the time that the leukoreduced apheresis PLT unit obtained from the human has been stored.

10. The method of claim 7, wherein the measurements performed are selected from the group consisting of mass spectrometry, enzymatic assay, and enzyme-linked immunosorbent assay (ELISA).

11. The method of claim 10, wherein the measurements are performed by a mass spectrometry technique selected from the group consisting of gas-chromatography/mass spectrometry (GC/MS), and liquid chromatography-tandem mass spectrometry (LC/MS/MS).

12. The method of claim 7, wherein the levels of the one or more biomarkers selected from the group consisting of adenine, C-glycosyltryptophan, and andro steroid monosulfate 2 in the test aliquot are 2-200 fold higher than the corresponding levels of the same biomarkers in the control aliquot.

* * * * *